United States Patent [19]

Scheper et al.

[11] Patent Number: 4,777,269

[45] Date of Patent: Oct. 11, 1988

[54] 7-PHENYLACETIC ACID-4-ALKYL-COUMARINYL AMIDES USEFUL IN FLUOROMETRIC DETERMINATION OF THE ACTIVITY OF HYDROLASES

[75] Inventors: Thomas Scheper, Hanover; Martina Weiss, Isernhagen; Karl Schügerl, Hemmingen, all of Fed. Rep. of Germany

[73] Assignee: European Atomic Energy Community, Luxembourg

[21] Appl. No.: 44,260

[22] Filed: Apr. 30, 1987

[30] Foreign Application Priority Data

Apr. 30, 1986 [DE] Fed. Rep. of Germany ....... 3614647

[51] Int. Cl.⁴ .......................................... C07D 311/16
[52] U.S. Cl. ....................... 549/288; 435/18
[58] Field of Search ........................ 549/288

[56] References Cited

U.S. PATENT DOCUMENTS

| | | | |
|---|---|---|---|
| 2,881,186 | 4/1959 | Häusermann | 549/288 |
| 3,352,885 | 11/1967 | Schelihammer et al. | 549/288 |
| 4,388,233 | 6/1983 | Bissell et al. | 549/288 |
| 4,409,140 | 10/1983 | Smith et al. | 549/288 |

FOREIGN PATENT DOCUMENTS 108974 9/1978 Japan ................................ 549/288

*Primary Examiner*—Jane T. Fan
*Attorney, Agent, or Firm*—Sughrue, Mion, Zinn, Macpeak, and Seas

[57] ABSTRACT

7-Phenylacetic acid-4-alkyl-coumarinyl amides having the formula

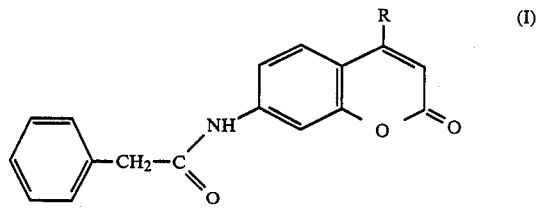

wherein R is alkyl having 1 to 4, in particular 1 to 2 carbon atoms, optionally substituted by one or more halogen atoms, in particular fluorine atoms, especially methyl or trifluoromethyl, are suitable substances for the fluorometric determination of the activity of hydrolases, in particular of penicillin G-acylase, since by the enzymatic reaction they provide cleavage products which in regard to their fluorescence properties differ drastically from those of the substrate. They can be used in processes for the fluorometric determination of the activity of hydrolases, in particular of penicillin G-acylase.

7 Claims, 3 Drawing Sheets

7-PHENYLACETIC ACID-4-ALKYL-COUMARINYL AMIDES USEFUL IN FLUOROMETRIC DETERMINATION OF THE ACTIVITY OF HYDROLASES

FIELD OF THE INVENTION

The invention relates to new 7-phenylacetic acid-4-alkylcoumarinyl amides of the general formula (I) below, in particular to the new compounds 7-phenylacetic acid-4-methylcoumarinyl amide (PMC) and 7-phenyl-acetic acid-4-trifluoromethyl-coumarinyl amide (PFC), to processes for their preparation and their use in processes for the fluorometric determination of the activity of hydrolases, in particular of acylases, especially of penicillin G-acylase.

BACKGROUND OF THE INVENTION

Penicillin G-acylase is needed in great amounts for the industrial production since it cleaves penicillin to produce 6-amino-penicillanic acid (6-APA). The 6-amino-penicillanic acid is a starting material for a broad range of semi-synthetic penicillins which in part can be synthesized with this enzyme. The enzyme is produced by microorganisms. The production of the enzyme is obtained for instance in genetic modified cells or by the induction of *E. coli* strains by phenyl acetic acid.

The protons which are released from penicillin G by the enzymatic cleavage can be used titrimetically for the determination of the activity. It is also possible to react the obtained 6-amino-penicillanic acid with p-dimethylamino-benzaldehyde (p-DMABA) to form a yellow coloured Schiff's base which can be determined photometrically.

Another photometric assay resides in the enzymatic cleavage of the 6-nitro-3-phenylacetamido-benzoic acid (NIPAB). The 3-amino-6-nitrobenzoic acid produced by the cleavage can be determined photometrically.

However, these known processes are less suited for the determination of low activities of penicillin G-acylase.

Therefore, several efforts have been made to find a fluorescence substrate for the penicillin G-acylase satisfying the following conditions:

(a) the cleavage product of the enzymatic reaction in regard to its fluorescence properties should be different from those of the substrate as far as possible,
(b) since penicillin G-acylase has a broad activity spectrum for phenylacetic acid amides, the substrate should have a phenylacetic acid radical since this radical seems to be important for the development of an activity against the substrates; and
(c) the fluorescence excitation should be in the ultraviolet range (mercury lamp) or in a range of an argon ion laser (488 nm).

Therefore, a fluorescing amine is desired which can easily be reacted with phenyl acetic acid to form a product for which the enzyme has a sufficient activity.

From U.S. Pat. No. 3,741,876 a fluorometric process for the determination of the activity of an enzyme is known wherein an enzyme and a solid substrate supported on an inert silicone matrix are reacted with each other to form a fluorescing material wherein the variation of the fluorescence with the time is measured to determine the concentration of one of both reactants. In this process dehydrogenases, oxidases, phosphatases, uricase, cholinesterase and lipase may be used as enzymes.

From EP No. 0 037 583 a process for the fluoremetric determination of the activity of fat degrading enzymes in samples containing these enzymes is known wherein the sample is combined with a substrate containing the compound which reacts with the enzyme to be tested, the substrate is excitated at a specific excitation wavelength of the corresponding fluorescing groups and the variation of the fluorescence intensity of the substrate under the action of the enzyme per time unit is measured at a specific emission wavelength of the fluorescing group, the extent of the variation being directly proportional to the enzyme activity of the sample. In this case triacyl glycerols are used as substrates which are cleaved by lipase to form free fatty acid, glycerides and glycerol.

From EP No. 0 018 112 a process for the determination of the presence of an enzyme in a biological liquid is known wherein the liquid is contacted with a synthetic chromogenic substance, the substrate containing the liquid is incubated to effect an enzymatic hydrolysis and the chromophore in the obtained hydrolyzate is determined fluorometrically. In this known process an amino acid derivative of 7-amino-4-trifluoromethyl-coumarin is used as chromogenic substrate. This process in the first place is suited for the determination of proteinase enzymes.

These known processes, too, are not suited for the qualitative and quantitative assay of penicillin G-acylase by fluorometry, in particular, at a low activity of the penicillin G-acylase.

The object of the invention was to find a chromophoric substrate satisfying the above conditions(a) to (c) and thus being suitable for the qualitative and quantitative assay of the penicillin G-acylase, in particular at a lower activity thereof.

SUMMARY OF THE INVENTION

Now it has been found that this object can be achieved according to the present invention by new 7-phenylacetic acid-4-alkyl-coumarinyl amides having the following formula (I) which are suited in an excellent manner for the qualitative and quantitative fluorometric determination of penicillin G-acylase and of other hydrolases, in particular of other acylases.

The subject-matter of the present invention are new 7-phenylacetic acid-4-alkyl-coumarinyl amides of the general formula

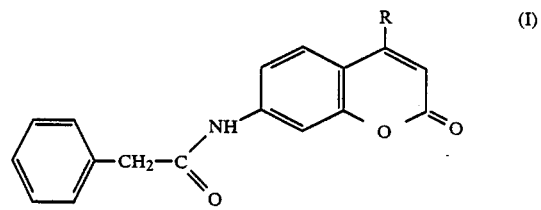

wherein R is alkyl having 1 to 4, in particular 1 to 2 carbon atoms, optionally substituted by one ore more halogen atoms, in particular fluorine atoms.

Particular advantageous compounds are those of the above general formula (I) wherein R is methyl or trifluoromethyl.

DETAILED DESCRIPTION OF THE INVENTION

The 7-phenylacetic acid-4-alkyl-coumarinyl amides of the present invention by the enzymatic reaction with hydrolases, in particular acylases, especially penicillin G-acylase, provide cleavage products which differ drastically in regard to their fluorescence properties from those of the substrate and the fluorescence excitation of which being in the ultraviolet range (mercury lamp) or in the range of an argon laser (488 nm).

In this connection particularly suitable are 7-phenyl-acetic acid-4-methyl-coumarinyl amide (PMC) and 7-phenyl-acetic acid-4-trifluoromethyl-coumarinyl amide (PFC) which can be cleaved by penicillin G-acylase according to the following reaction scheme:

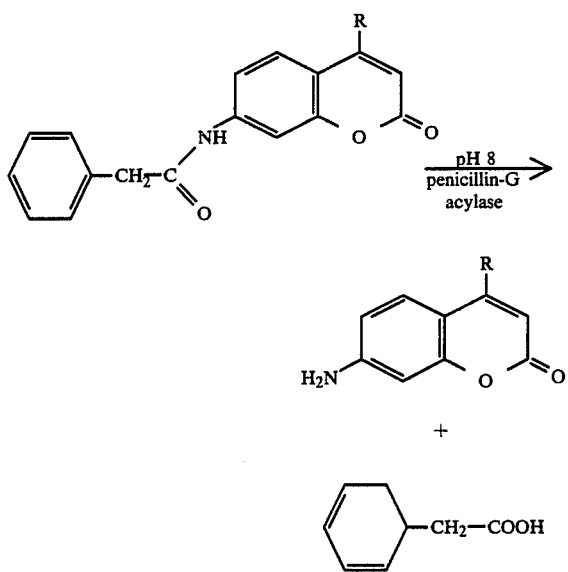

to form the free amino-coumarins. This reaction can be carried out at pH 8 in a 50 mM potassium phosphate buffer and can be followed in a spectral fluorometer (Schoeffel). An excitation wavelength of 365 nm can be used for both the substrates. The emission wavelength for the enzymatic test with PMC is 440 nm and for the test with PFC is 495 nm.

As can be seen from FIG. 1 of the enclosed drawings, the substrate and the reaction products are very much different. The diagrams show the emission spectra of the test mixture (3 μg/ml of substrate, pH=8, 50 mM K-P-buffer (excitation 365 nm)).

Both substrates can be used in a fluorescence-enzyme-test wherein the increase of the fluorescence intensity with the time at various penicillin G-acylase concentrations is determined. The obtained results are shown in FIGS. 2 and 3 of the attached drawings.

A further subject-matter of the present invention is a process for the preparation of the 7-phenyl-acetic acid 4-alkyl-coumarinyl amides having the above general formula (I) the process being characterized in that a 7-amino-4alkylcoumarin of the general formula

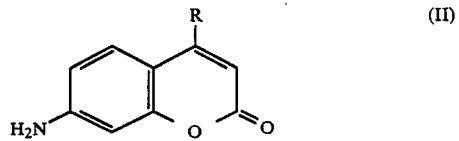

wherein R is defined as above is reacted in solution with phenyl-acetylchloride in the presence of a base, i.e. of a proton acceptor, under anhydrous conditions, and from the obtained reaction product the 7-phenylacetic acid-4-alkylcoumarinyl amide is precipitated and purified.

According to a preferred embodiment of the present invention the 7-amino-4-alkyl-coumarin having the above formula (II), wherein R is methyl or trifluoromethyl, is dissolved in dioxane and added with a slight excess of pyridine while stirring and then phenylacetylchloride in a slight excess, also dissolved in dioxane, is added dropwise. The obtained reaction mixture is stirred for 3 hours and then poured on ice, then slightly acidified with HCl, filtered and washed with distilled water until the filtrate is neutral and the amide obtained as a product is finally recrystallised from ethanol and dried.

To carry out the process of the invention any solvents can be used, f.i. those described in "Organikum", VEB Deutscher Verlag der Wissenschaft, Berlin, 1975, 14. Auflage, section "Säureamidherstellung". The solvents have to be absolutely anhydrous, but must be miscible with water to precipitate the product.

Besides pyridine any bases can be used as proton acceptors in carrying out the process of the invention (see "Organikum", section "Säureamide").

The concentration in which the starting materials ar each dissolved in the solvent depends on the solubility of each of the fluorophosphores, a 10% solution being preferred. An optimal concentration of PMC and PFC is 1 mmol in 60 ml of dioxane.

The concentration of proton acceptor (pyridine) and phenylacetyl chloride is at least equimolar, preferably slightly higher, the optimum being an excess of 1,1 times the stochiometrical amount.

The temperature range to carry out the process of the present invention is not particularly critical. In general it ranges from the melting point to the boiling point of the solvent, however, the decomposition temperature of the reactants is to be considered. It is preferred to use a temperature of from 15° to 35° C., in particular from 20° to 25° C.

The reaction time in general is 10 minutes to 24 hours, preferably 30 minutes to 6 hours, especially 3 hours.

In carrying out the process of the present invention a 2-neck-flask provided with a drying tube and a dropping means in a water bath having a temperature of from 20° to 25° C. is charged with the alkyl-coumarin, while stirring with a magnetic stirrer dioxane is added, then pyridine is added whereby a precipitate of a pyridine-aminocoumarin-complex is formed. Then the acetyl chloride, dissolved in dioxane, is added dropwise.

The synthesis has to be carried out under absolutely anhydrous conditions since otherwise the used acetyl chloride is hydrolized. The obtained reaction mixture is poured on an equal amount of ice, 30% HCl is added dropwise until no more precipitate is formed. After the dissolution of the ice further HCl is added until no more precipitate is formed, then it is filtrated conveniently by using a suction filter, rinsed with ice-cooled water and recrystallized from ethanol twice and finally dried sharply.

The compounds obtained in carrying out this process are sensitive to light and hydrolysis and can be identified by their IR and NMR spectra.

A further subject-matter of the present invention is the use of the 7-phenylacetic acid-4-alkyl-coumarinyl amides of the above formula (I), in particular the use of 7-phenylacetic acid-4-methyl-coumarinyl amide (PMC) and of 7-phenylacetic acid-4-trifluoromethyl-coumarinyl amide (PFC) for the fluorometric determination of the activity of hydrolases, in particular of acylases, especially of penicillin G-acylase.

A fluorometric process for the determination of the activity of hydrolases, in particular of penicillin G-acylase, which constitutes a further subject-matter of the present invention, is characterized in that a 7-phenylacetic acid-4-alkylcoumarinyl amide of the formula (I) is dissolved in a suitable solvent and diluted with a buffer to a concentration of from 1 to 10 µg/ml, preferably 2 to 6 µg/ml, especially 3 µg/ml, the obtained mixture is measured in a spectral fluorometer (λ440 to 495 nm) in regard to the background signal, then the reaction is started by the addition of 10 to 100 µml of the test mixture to be examined and followed in the spectral fluorometer to determinethe activity of the enzyme by the linear initial increase of the fluorescence/time-diagram. During the test the pH-value is maintained in general in the range of from 7.0 to 9.5, preferably 7.5 to 9.0, optimally 8.0 to 8.5. As buffer any buffer can be used, a K-P-buffer or a Tris buffer being particularly preferred. The concentration of the 7-phenylacetic acid-4-alkyl-coumarinyl amide, in particular of the compounds PFC and PMC, used according to the present invention for carrying out the fluorometric test in general is in the range of from 10 to 250 mmol, preferably 30 to 100 mmol, especially 50 mmol, however, the capacity of the buffer has to be considered. By the way, the concentration of the substrate is dependent on the solubility and on the kinetic data; for PMC and PFC conveniently it is in the range of from 1 to 10 µg/ml, preferably between 2 and 6 µg/ml, especially at 3 µg/ml.

A further subject-matter of the present invention is a process for the detection of the activity of intracellular hydrolase, in particular of penicillin G-acylase, which is characterized in that the microorganism cells containing hydrolase are separated from the culture medium and added to a solution of a 7-phenylacetic acid-4-alkyl-coumarinyl amide of the formula (I), then the fluorescence emission caused by the enzymatic reaction product 7-amino-4-alkyl-coumarin enriched in the cells is observed in a fluorescence microscope at 450 to 495 nm.

For carrying out this process also so-called "trapping reagents" may be used, which are substances which reduce considerably the solubility of the fluorophore released in the cells, such as salts or substances which, after the chemical reaction with fluorine, provide hardly soluble products (see Dolbeare, Smith, "J. Clin. Chem.", 23 (1977) and F. Scrienc, J. Bailey, "3rd Europ. Cong. Biotechn. München, 1984).

According to a further subject-matter of the present invention the activity of intracellular hydrolases, in particular of intracellular penicillin G-acylase, can be determined by separating the microorganism cells containing the hydrolase from the culture medium, fixing the cells in 50% ethanol to make the cell membrane permeable for the reaction product 7-amino-4-alkyl-coumarin, by introducing 20 µl of, the the cell suspension into a solution of a 7-phenylacetic acid 4-alkylcoumarinyl amide of the formula (I) and measuring the intensity of the fluorescence due to the reaction which intensity is proportional to the concentration of the product permeated into the solution in a spectral fluorometer as a function of the measured time and calculated back to the activity of the enzyme.

For carrying out this process of the invention all microorganisms may be used wherein penicillin G-acylase can be detected.

While during carrying out this fluorometric process the excitation wavelength is in the range of from 380 to 400 nm (PMC) and from 420 to 440 nm (PFC)respectively, the emission wavelength after the addition of the enzyme for PMC is in the range of from 400 to 520 nm, preferably from 420 to 460 nm, especially at 440 nm, and for PFC is in the range of from 440 to 550 nm, preferably from 480 to 520 nm, especially at 495 nm.

The invention now is illustrated in detail in connection with the attached drawings.

FIG. 1 shows emission spectra of the substrates PMC (FIG. 1a) and PFC in a buffer solution (50 mM phosphate buffer, pH 8); (FIG. 1b)

FIGS. 2 and 3 show the calibration curves for both of the substrates PMC (PMC:1 µg/ml, 50 mM buffer, 0% ethanol, pH 8) and PFC (PFC:3 µg/ml, 50 mM buffer, 5% ethanol, pH 8) (excitation wavelength 365 nm; emission wavelength 440 nm for PMC and 492 nm for PFC, respectively);

The composition of the substrate solutions is indicated in the diagrams of the attached drawings. In the tests 3 ml of each of the substrate solutions are added with 10 µl of the enzyme solution. The increase of the luorescence (at the indicated values) are followed for 3 minutes. The increase of the fluorescence with the time as a function of the enzyme concentration in the test mixture is plotted in the diagrams.

The calibration curves are linear in the range of from 20 to about 300 µU/ml for PMC and for PFC corresponding to a volume capacity of the injected solution of the enzyme of from 6.0 to 90 mU/ml.

The values for the PFC test are easily reproduceable since the solution of the substrate (5% ethanol) can be prepared more accurately. For the preparation of solutions of the substrate without ethanol about 24 hours are need to dissolve 1 mg of the substrate in 1 l of the buffer. The fluorometric test is particularly suited for the determination of low activities of penicillin G-acylase.

During the tests it has been observed repeatedly that the conversion rate of the reaction decreases at higher substrate concentrations. Therefore, research work for the determination of the kinetic parameters (Vmax and $K_M$) of this reaction system had to be carried out.

The enzyme concentration in the test was kept constant and the substrate concentration (50 mM K-P-buffer 5% ethanol for both substrates) was varied.

Figure 1A:
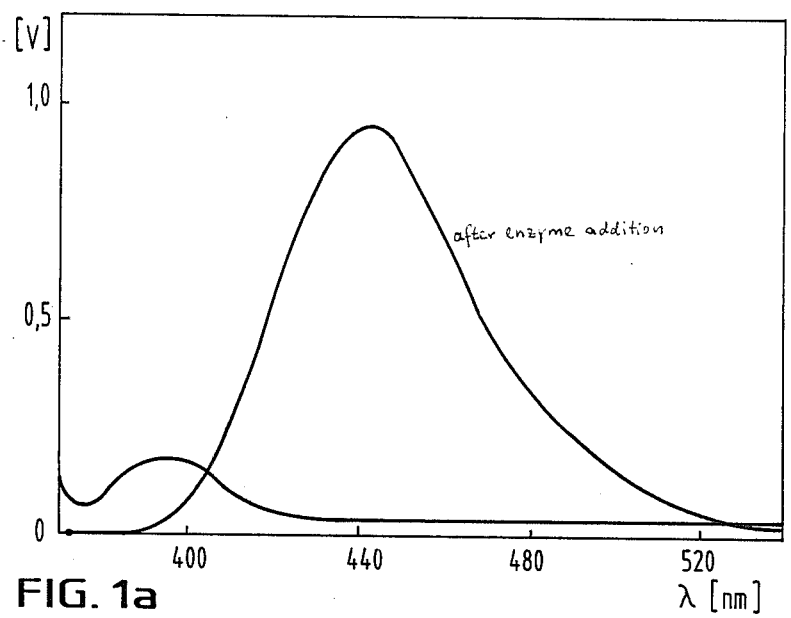
Figure 1B:
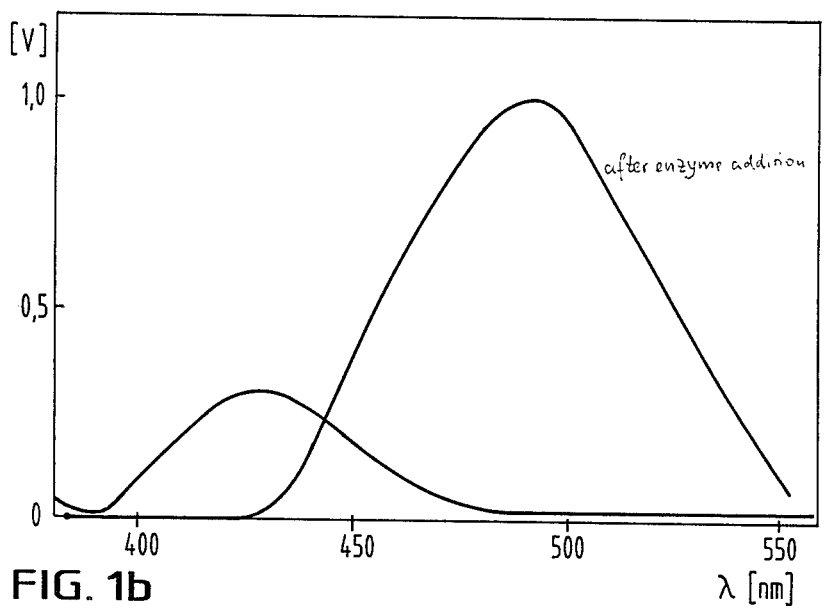
Figure 2:
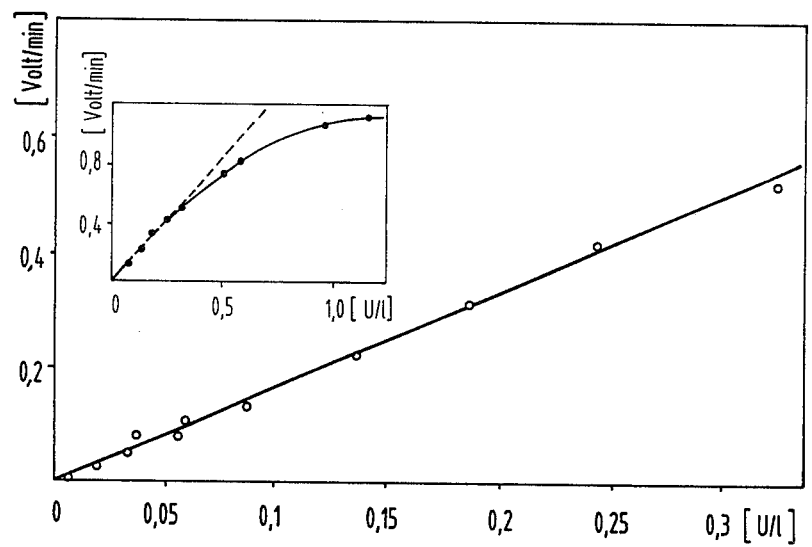
Figure 3:
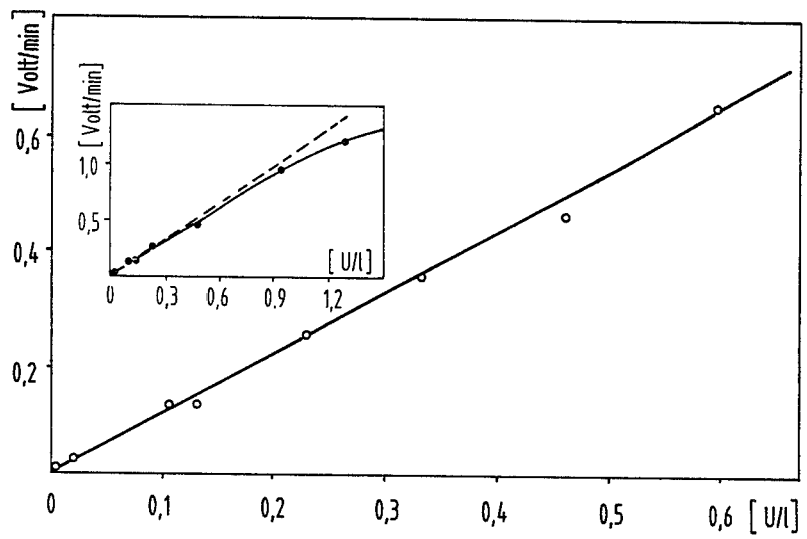
Figure 4:
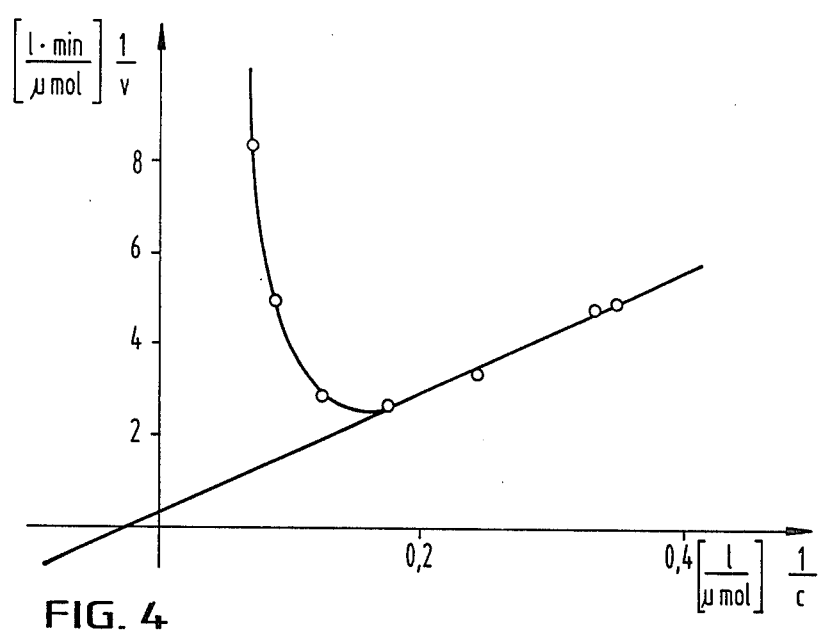
FIG. 4 shows the Lineweafer-Burg-plot for the PFC test.

FIG. 4 shows the Lineweafer-Burg-plot for the PFC derivative. The course of the curve unequivocally indicates a substrate inhibition (see H. U. Bergemeyer, "Grundlagen der enzymatischen Analyse", Verlag Chemie/Weinheim, 1976).

In order to achieve a quick and well measurable conversion of the phenylacetic acid-coumarinyl amides, therefore, a suitable substrate concentration has to be present in the test mixture. This concentration is about 3 μg/ml (50 mM K-P-buffer; 5% ethanol) for both substrates. The parameters Vmax and $K_M$ for the described test conditions are as follows:

$$PMC: V_{max} = 11{,}07 \frac{\mu mol}{1\ min}\ ;\ K_M = 83{,}1 \frac{\mu mol}{1}$$

$$PFC: V_{max} = 3{,}33 \frac{\mu mol}{1\ min}\ ;\ K_M = 44{,}7 \frac{\mu mol}{1}$$

The PFC derivative is particularly suited for carrying out the fluorometric tests with microorganisms. After the enzymatic cleavage the fluorescence emission is at 495 nm, i.e. in the visible (green) area. This wavelength can be well observed by means of a fluorescence microscope (Diawert provided with a fluorescence equipment of Leitz Company). The microorganisms having a intracellular penicillin G-acylase activity may easily and specifically be coloured with this substrate and observed in the fluorescence microscope. The reaction product 7-amino-4-(trifluoromethyl)coumarin forms intracellularily and is enriched there to a certain extent.

Figure 5:
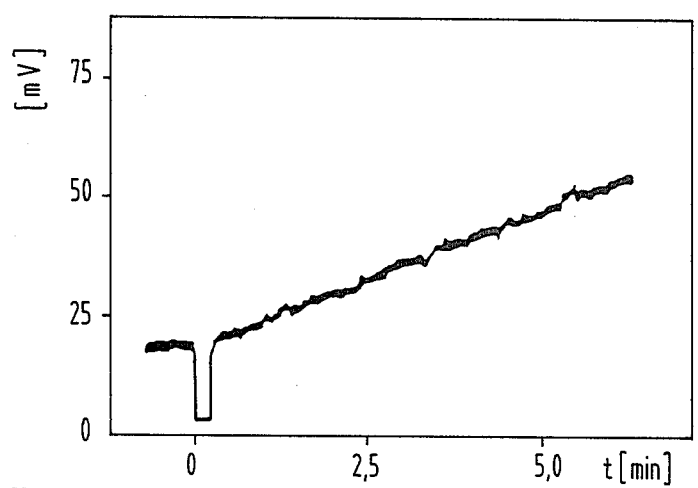
FIG. 5 shows the fluorometric test with E. coli cells containing penicillin G-acylase.

In order to follow this reaction also in the spectral fluorometer E. coli cells containing penicillin G-acylase were fixed for 10 minutes in cold 50% ethanol. Thereby the cell wall has been made permeable in such an extent that it was permeable both for the substrate and for the product of the reaction. 20 μl of the cell suspension were injected into a PFC solution and followed fluorometrically (see FIG. 5).

The volume activity of the suspension determined according to the NIPAB-method was considerably below 100 mU/ml, the volume activity determined according to the PFC-method was 45 mU/ml. Tests carried out with higher volume activities showed that both methods were in good coincidence.

The coumarin derivatives of the present invention, in particular PFC and PMC, are suitable as substrates for the fluorometric determination of hydrolases, in particular of acylases, especially of penicillin G-acylase. The reaction upon which the determination method is based, can be illustrated by the following scheme:

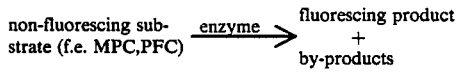

non-fluorescing substrate (f.e. MPC, PFC) —enzyme→ fluorescing product + by-products The optimal concentration range of the substrates (PMC, PFC) in the test is 3 μg/ml (5% ethanol). Higher concentrations are not useful because of a substrate inhibition. The test allows also to measure low concentrations of the enzyme—even intracellularily. For the carrying out of this test essentially all fluorophores having an amino group can be used, however, it is to be considered that the synthesis product exhibits another fluorescence behaviour than the free fluorophore after the enzymatic cleavage.

The reaction of the present invention is specific to penicillin G-acylase. However, it may also be applied to other hydrolases, in that case instead of the phenylacetyl group specific to penicillin G-acylase a corresponding group specific to this other enzyme has to be introduced.

The yields obtained in the preparation of the 7-phenylacetic acid-4-alkyl-coumarinyl amides of the invention, in particular of PFC and PMC, were in the range of from 50 to 80% at a high product purity (NMR, IR). Both of the last mentioned substrates exhibit a low solubility in aqueous solutions (below 1 mg/l). However, this problem may be overcome by dissolving the substrate at first in pure ethanol and then diluting it with the corresponding buffer to a mixture with 5% ethanol. In this manner concentrations of 6 mg/l can be achieved.

The present invention is illustrated in detail in the following examples, however without being limited thereto.

EXAMPLE 1

Preparation of the coumarinyl derivatives PMC and PFC

The following chemicals were used:

| | |
|---|---|
| 7-amino-4-methylcoumarin | (Aldrich Chemical Co.) |
| 7-amino-4-(trifluoromethyl)coumarin | (Aldrich Chemical Co.) |
| phenylacetyl chloride | (Fluka) |
| dioxane, anhydrous | (Merck) |
| pyridine, anhydrous | (Merck) |
| ethanol | (Merck) |
| 32% hydrochloric acid | (Merck) |

A 2-neck-flask provided with a drying tube and a dropping means in a water bath of a temperature of from 20° to 25° C. is charged with 1 mmol coumarin, and 60 ml of dioxane are added while stirring (with a magnetic stirrer) to dissolve the coumarin. Then 1,1 mmol pyridine are added while stirring, whereby a precipitate of a pyridine-aminocoumarin-complex is formed. Then 1,1 mmol phenylacetyl chloride, dissolved in 2 ml dioxane, are added dropwise within 2 minutes. The reaction mixture is stirred for 3 hours and then poured on an equal amount of ice, the mixture is acidified with 321 % HCl until no more precipitate is formed. After the dissolution of the ice further HCl is added until no more precipitate is formed, then it is filtered using a sucking filter and washed with ice-cooled water until the filtrate is neutral. The obtained amide is twice recrystallized from ethanol (about 150 ml for PMC and about 30 ml for PFC) and dried sharply. The obtained coumarinyl derivatives have to be stored in a refrigerator under anhydrous and light-shielded conditions. The yields were 67 to 77% for PMC and 52 to 57% for PFC.

EXAMPLE 2

Test for the determination of the activity of penicillin G-acylase by using the coumarinyl derivatives PMC and PFC The test mixture contains 3 μg/ml of the coumarinyl derivative as obtained in example 1, dissolved in 50 mM of a potassium-phosphate-buffer (pH 8, 5% ethanol).

At first a solution of the coumarinyl derivative in ethanol is prepared and diluted with the phosphate buffer according to the concentration values. 3 ml of the mixture are measured in a fluorescence cuvette in a spectral fluorometer (λ=440 nm for PMC; λ=495 nm for PFC) in regard to the background signal.

The reaction is started (while stirring) by the addition of 10 to 100 μl of the sample and followed. The activity of the enzyme can be estimated from the linear initial increase of the fluorescence/time-diagram after a corresponding calibration has been made.

EXAMPLE 3

Detection of the activity of intracellular penicillin G-acylase

*E. coli* cells containing penicillin G-acylase are separated from the nutrition medium (for example by centrifugation) and introduced into a PFC solution as obtained in example 2. The fluorescence emission caused by the enzymatic reaction product 7-amino-4-(trifluoromethyl)coumarin enriched in the cells is observed in a fluorescence microscope (Leitz, Diawert provided with a fluorescence equipment) at 495 nm.

EXAMPLE 4

Determination of the activity of intracellular penicillin G-acylase

*E. coli* cells containing penicillin G-acylase are separated from the nutrition medium (for example by centrifugation) and are fixed for 10 minutes in cold 50% ethanol in order to make the cell membrane permeable also for the product of PFC, namely 7-amino-4-(trifluoromethyl)coumarin.

20 μl of the cell suspension are injected into a PFC solution as obtained in example 2 and the fluorescence intensity, proportional to the concentration of the product permeated into the solution, is measured in a spectral fluorometer as a function of the time (see FIG. 5) and calculated back to the activity of the enzyme.

EXAMPLE 5

Determination of the activity of intracellular penicillin G-acylase

The process described in example 3 is repeated by using "trapping reagents", i.e. by using substances which reduce substantially the solubility of the fluorophore released in the cells, such as salts (like NaCl or substances which after the chemical reaction with fluorine provide hardly soluble products.

The obtainable high proportion of up to 50% ethanol in the dying solution after carrying out the reaction is diluted considerably after the reaction for 30 minutes after the centrifugation by a 0.9% NaCl solution. In this way the solubility of the reaction product in the cells is reduced substantially.

We claim:

1. A 7-phenylacetic acid-4-alkyl-coumarinyl amide represented by the formula (I):

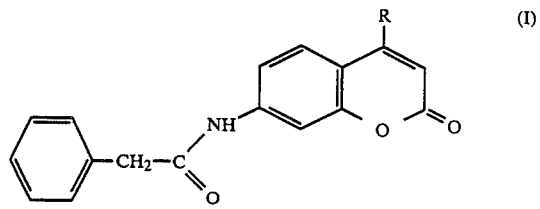

wherein R represents an alkyl having 1 to 4 carbon atoms, which are unsubstituted or substituted by 1 or more halogen atoms.

2. The compounds according to claim 1, characterized in that in formula (I) R is methyl or trifluoromethyl.

3. The amide according to claim 1, wherein R represents an alkyl group having 1 to 2 carbon atoms.

4. The amide according to claim 3, wherein the halogen atoms are fluorine atoms.

5. The amide according to claim 1, wherein the halogen atoms are fluorine atoms.

6. 7-Phenylacetic acid-4-methyl-coumarinyl amide (PMC).

7. 7-Phenylacetic acid-4-trifluoromethyl-coumarinyl amide (PFC).

* * * * *